US011160465B2

(12) United States Patent
Guy, III

(10) Patent No.: US 11,160,465 B2
(45) Date of Patent: Nov. 2, 2021

(54) WRAP AND METHOD TO PROVIDE COMPRESSION, AND PROTECTION TO BODY PART OF USER

(71) Applicant: Thomas Guy, III, Brooklyn, NY (US)

(72) Inventor: Thomas Guy, III, Brooklyn, NY (US)

(73) Assignee: Boa Wrapz, LLC

( * ) Notice: Subject to any disclaimer, the term of this patent is extended or adjusted under 35 U.S.C. 154(b) by 0 days.

(21) Appl. No.: 16/586,709

(22) Filed: Sep. 27, 2019

(65) Prior Publication Data
US 2020/0022585 A1 Jan. 23, 2020

Related U.S. Application Data

(63) Continuation-in-part of application No. 15/615,842, filed on Jun. 7, 2017.

(51) Int. Cl.
*A61B 5/00* (2006.01)
*A61B 5/022* (2006.01)
(Continued)

(52) U.S. Cl.
CPC ............ *A61B 5/022* (2013.01); *A43B 3/0005* (2013.01); *A61B 5/02141* (2013.01);
(Continued)

(58) Field of Classification Search
CPC .... A61F 13/107; A61F 13/108; A61F 13/062; A61F 5/01; A61F 5/013; A61F 5/0111; A61F 5/012; A61F 2005/0188; A61B 5/11; A61B 5/02141; A61B 5/0295; A61B 5/022; A61B 5/742; A61B 2505/09;
(Continued)

(56) References Cited

U.S. PATENT DOCUMENTS

2002/0042583 A1* 4/2002 Barak ..................... A61F 5/012
601/1
2008/0146975 A1* 6/2008 Ho ......................... A61H 31/00
601/44
(Continued)

FOREIGN PATENT DOCUMENTS

WO wo2009014644 * 1/2009

*Primary Examiner* — Steven O Douglas
(74) *Attorney, Agent, or Firm* — The Law Firm of Andrea Hence Evans, LLC

(57) ABSTRACT

Disclosed is a wrap which is removably attached with a body part of a user to provide compression, and protection. The wrap includes first sensing unit, second sensing unit, movement unit, adjuster unit, and a power source. The first sensing unit senses the physiological state of the user's body. The second sensing unit measures the dimension of the body part of the user. The body part is selected from at least one of: wrist, ankle, lower back, knee and/or combination thereof. The movement unit receives sensed information from first sensing unit, and second sensing unit to support an inflate mechanism and deflate mechanism to provide desired compression to the body part of the user. The adjuster unit configured with the movement unit to engage or disengage the wrap from the body part of the user. The power source which further includes a rechargeable battery powers the first sensing unit, second sensing unit, movement unit, and the adjuster unit.

14 Claims, 8 Drawing Sheets

(51) Int. Cl.
*A43B 3/00* (2006.01)
*A61B 5/021* (2006.01)
*A61F 5/01* (2006.01)

(52) U.S. Cl.
CPC .............. *A61B 5/742* (2013.01); *A61F 5/012* (2013.01); *A61F 5/013* (2013.01); *A61F 5/0111* (2013.01); *A61B 2505/09* (2013.01); *A61F 2005/0188* (2013.01)

(58) Field of Classification Search
CPC ..... A61B 5/021; A61B 5/02438; A61B 5/747; A61B 5/1118; A61B 2560/0214; A61B 5/6824; A61B 5/4528; A61B 5/1072; A61B 5/6806; A61B 5/6811; A61B 5/6807; A61B 5/6831; A61H 9/0078; A43B 3/0005; G16H 80/00
See application file for complete search history.

(56) References Cited

U.S. PATENT DOCUMENTS

| | | | |
|---|---|---|---|
| 2014/0070042 A1 | 3/2014 | Beers | |
| 2016/0220808 A1* | 8/2016 | Hyde | A61N 1/0452 |
| 2017/0312161 A1* | 11/2017 | Johnson | A41D 1/005 |
| 2018/0263517 A1 | 9/2018 | Kubo | |
| 2018/0289522 A1 | 10/2018 | Zhu | |
| 2018/0353347 A1* | 12/2018 | Guy, III | A61F 13/108 |

\* cited by examiner

WRAP AND METHOD TO PROVIDE COMPRESSION, AND PROTECTION TO BODY PART OF USER

TECHNICAL FIELD

The present invention is generally related to a wrap to be worn around the wrist or ankle to provide compression, and protection based on the sensed physiological and dimensional information of the user.

BACKGROUND

Generally, apparatus and methods are available in the prior art which enables a user to manually tighten the exercise gloves and shoes. The tightening mechanism of the existing prior arts are completely manual and doesn't utilizes the physiological parameters of the user such as blood pressure or heartbeat to provide optimal support around the body parts under strain while doing physical activities. Further the existing apparatus and methods can tighten or compress the body of the user up to a pre-defined dimension. These apparatuses are not designed to consider and measure the dimensions and size of the user's ankle/wrist in real time to provide optimal support around the body parts under strain while doing physical activities.

Therefore, there is a need of a wrap and a method to compress and to provide optimal support around the body parts under strain while doing physical activities by utilizing the accurate physiological information and the dimensional data. Further there is also a need of a wrap and a method which can automatically inflate and deflate to provide optimal support around the body parts under strain while doing physical activities.

Further limitations and disadvantages of conventional and traditional approaches will become apparent to one of skill in the art through comparison of described systems with some aspects of the present disclosure, as set forth in the remainder of the present application and with reference to the drawings.

SUMMARY OF THE INVENTION

A wrap which is removably attached with at least one of a body part of a user to provide compression, and protection is provided substantially, as shown in and/or described in connection with at least one of the figures, as set forth more completely in the claims.

The wrap includes a first sensing unit, a second sensing unit, a movement unit, an adjuster unit, and a power source. The first sensing unit senses the physiological state of the user's body. The second sensing unit measures the dimension of the body part of the user. In an embodiment, the body part is selected from at least one of: wrist, ankle, lower back, knee, and/or combination thereof. The movement unit receives the sensed information from the first sensing unit, and the second sensing unit to support an inflate mechanism and a deflate mechanism to provide desired compression to the body part of the user. The adjuster unit configured with the movement unit to engage or disengage the wrap from the body part of the user. The power source which further includes a rechargeable battery powers the first sensing unit, the second sensing unit, the movement unit, and the adjuster unit.

According to embodiments illustrated herein, there is provided a method for providing compression, and protection to at least one of a body part of a user. The method initiates with the step of sensing the physiological state of the user's body through a first sensing unit. The method further includes the step of measuring dimension of the body part of the user through a second sensing unit. In an embodiment, the body part is selected from at least one of: wrist, ankle, lower back, knee, and/or combination thereof. The method further includes the step of receiving the sensed information from the first sensing unit and the second sensing unit through a movement unit to support an inflate mechanism and a deflate mechanism to provide desired compression to the body part of the user. Further the method includes the step of engaging or disengaging the wrap from the body part of the user through an adjuster unit configured with the movement unit. Then the method includes the step of powering the first sensing unit, the second sensing unit, the movement unit, and the adjuster unit through a power source.

These features and advantages of the present disclosure may be appreciated by reviewing the following description of the present disclosure, along with the accompanying figures wherein like reference numerals refer to like parts.

BRIEF DESCRIPTION OF DRAWINGS

The accompanying drawings illustrate the embodiments of systems, methods, and other aspects of the disclosure. Any person with ordinary skills in the art will appreciate that the illustrated element boundaries (e.g., boxes, groups of boxes, or other shapes) in the figures represent an example of the boundaries. In some examples, one element may be designed as multiple elements, or multiple elements may be designed as one element. In some examples, an element shown as an internal component of one element may be implemented as an external component in another, and vice versa. Furthermore, the elements may not be drawn to scale.

Various embodiments will hereinafter be described in accordance with the appended drawings, which are provided to illustrate, not limit, the scope, wherein similar designations denote similar elements, and in which.

DETAILED DESCRIPTION

The present disclosure is best understood with reference to the detailed figures and description set forth herein. Various embodiments have been discussed with reference to the figures. However, those skilled in the art will readily appreciate that the detailed descriptions provided herein with respect to the figures are merely for explanatory purposes, as the methods and systems may extend beyond the described embodiments. For instance, the teachings presented and the needs of a particular application may yield multiple alternative and suitable approaches to implement the functionality of any detail described herein. Therefore, any approach may extend beyond certain implementation choices in the following embodiments.

Figure 1:
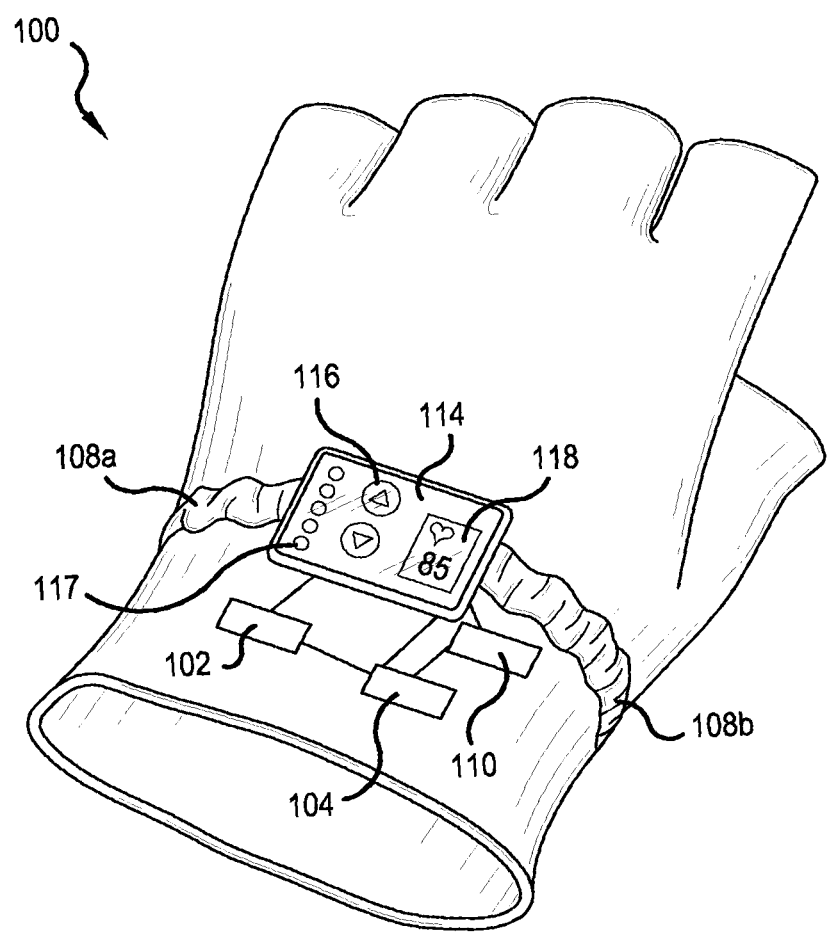
FIG. 1 illustrates an exemplary diagram of the wrap which is removably attached with the wrist of the user to provide compression, and protection, in accordance with at least one embodiment.

FIG. 1 illustrates an exemplary diagram 100 of the wrap which is removably attached with the wrist 204 of the user to provide compression, and protection, in accordance with at least one embodiment. The present wrap may have configured with either an exercise gloves, with an ankle shoe, lower back (preferably waist), and knee. The wrap 100 includes a first sensing unit 102, a second sensing unit 104, a movement unit 106, an adjuster unit 108 and a power source 110. The first sensing unit 102 senses the physiological state of the user's body. The second sensing unit 104 measures the dimension of the body part of the user. In alternative embodiments, the wrap can be configured to suitably fit a body party, including but not limited to the wrist 204, ankle, back, elbow, hip, shoulder, neck, knee or combination thereof.

Figure 2:
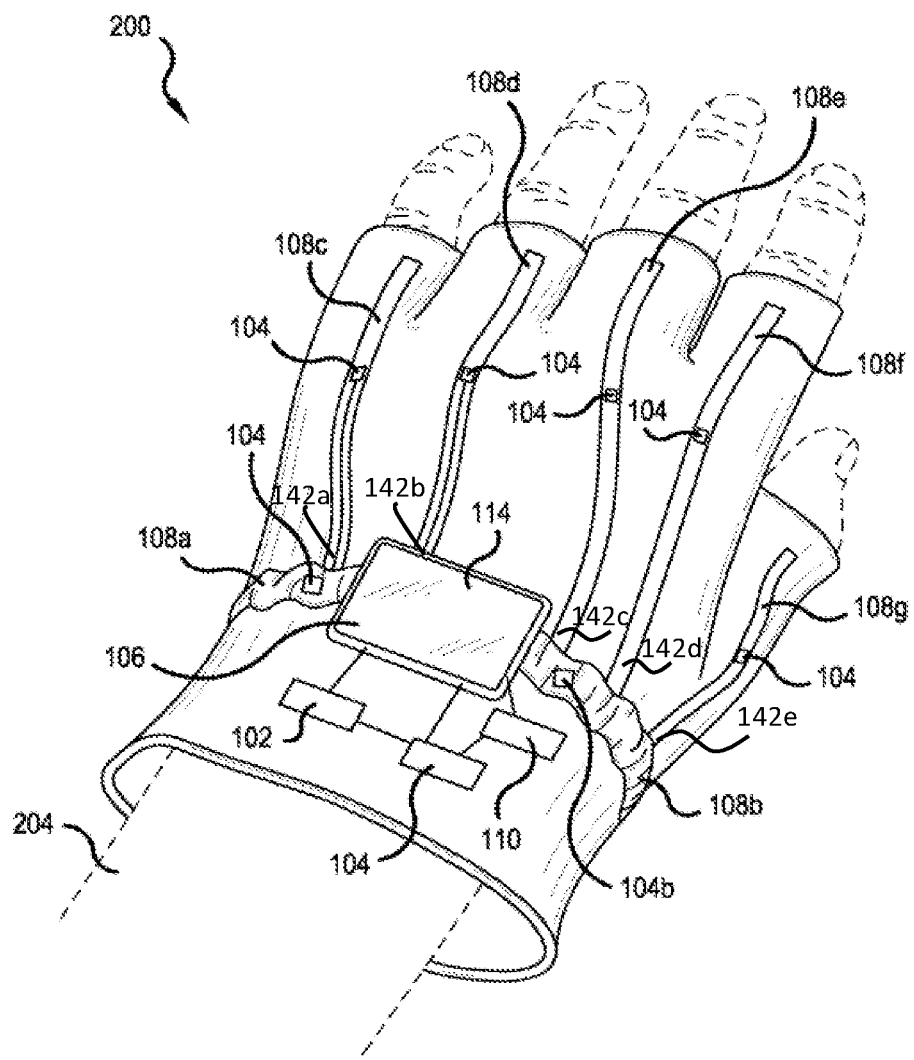
FIG. 2 illustrates a deflated view of the wrap of an alternative embodiment wherein the compression can be applied to the wrist and fingers.
Figure 3:
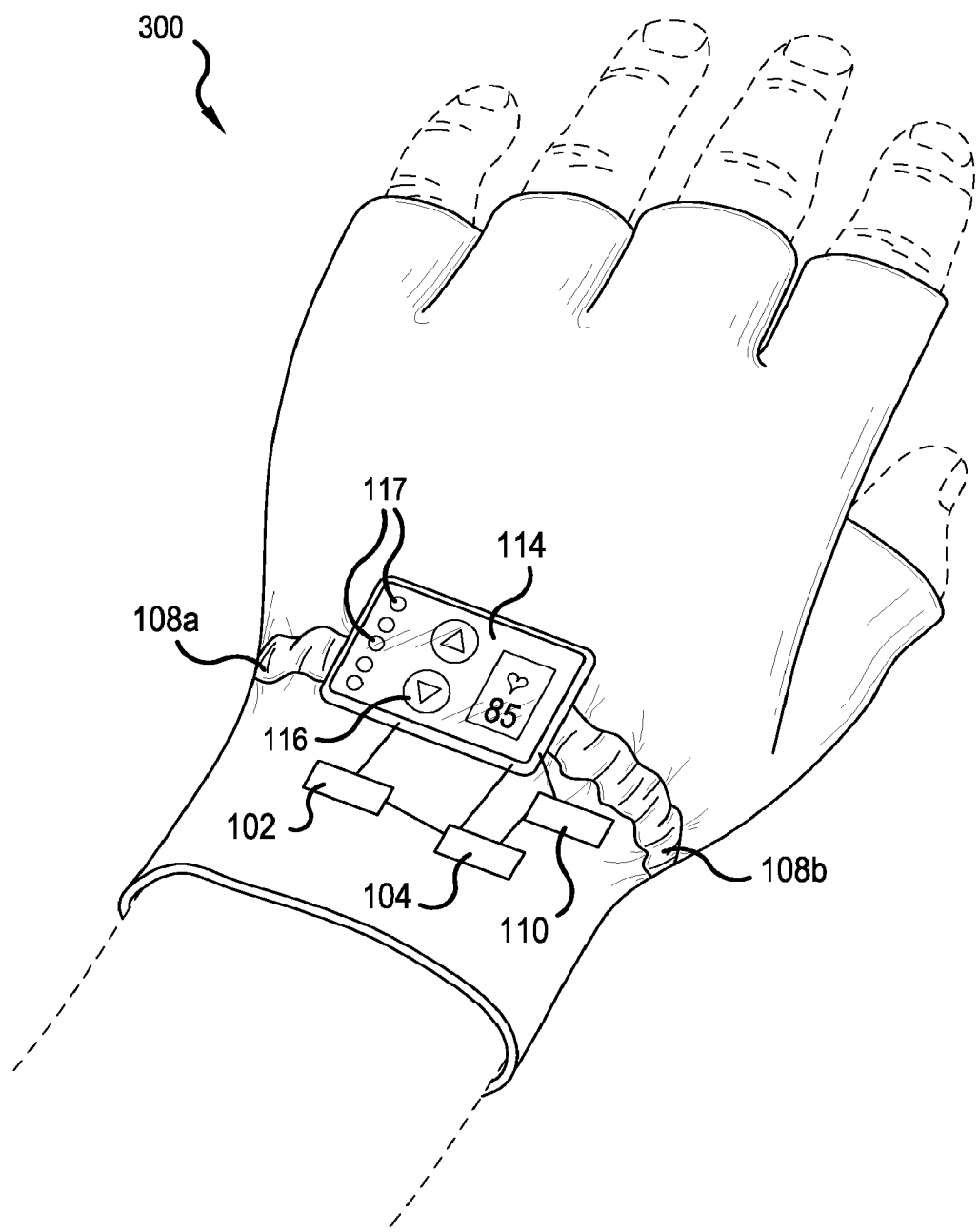
FIG. 3 illustrates an inflated view of the wrap worn around the wrist, in accordance with at the embodiment in FIG. 1.
Figure 6:
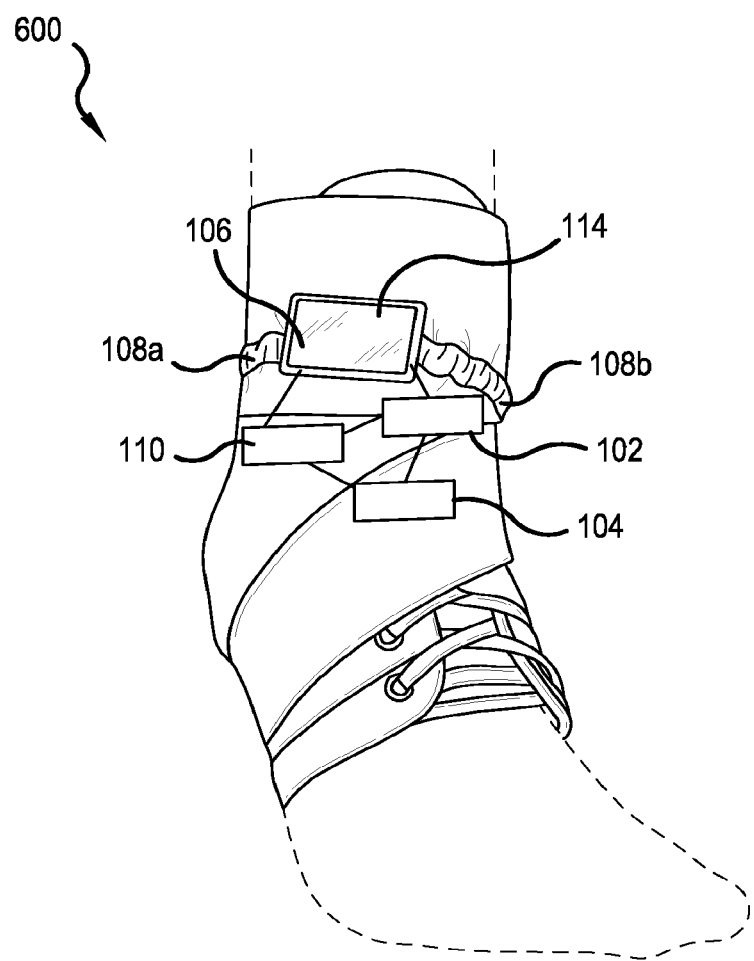
FIG. 6 illustrates another exemplary diagram of the wrap which is removably attached with the ankle of the user to provide compression, and protection, in accordance with at least one embodiment.

The movement unit 106 receives the sensed information from the first sensing unit 102, and the second sensing unit 104 to support an inflate mechanism and a deflate mechanism to provide desired compression to the body part of the user. FIG. 2 illustrates a deflated view 200 of the wrap worn around the wrist, in accordance with at least one embodiment. FIG. 2 is explained in conjunction with FIG. 1. The adjuster nit 108a, 108b configured with the movement unit 106 to engage or disengage the wrap from the body part of the user. As shown in FIG. 2, the adjuster unit 108, can comprise additional components (108c-108g) that can provide compression to fingers. Additional embodiments are considered wherein airflow from 108 can reach other portions of the body coupled to the wrap. For example, FIG. 6 depicts the wrap 600 covering the ankle of a patient. As depicted, the adjuster unit 108a and 108b circumscribe the top of the ankle. Similar to FIG. 2, the alternate embodiment of the wrap in FIG. 6 could include additional adjuster units (108c-108g) that can be oriented to extend to other regions of the ankle: such as the ball of the ankle or arch of the foot. FIG. 3 illustrates an inflated view 300 of the wrap worn around the wrist, in accordance with at least one embodiment. FIG. 3 is explained in conjunction with FIG. 1 and FIG. 2.

The power source 110 includes a rechargeable battery to power the first sensing unit 102, the second sensing unit 104, the movement unit 106, and the adjuster unit 108a, 108b. The movement unit 106 includes an air pump 132 to actuate on receiving the sensed information to provide support to the user while performing a physical activity, further the user may actuate the air pump manually. Similarly, the user can manually release any pressure by actuating a pressure release valve 133. In another aspect, the air pump 132 can be powered by an auxiliary motor integrated into the housing 114. The physiological state of the user's body includes blood pressure, and hear rate.

Figure 4:
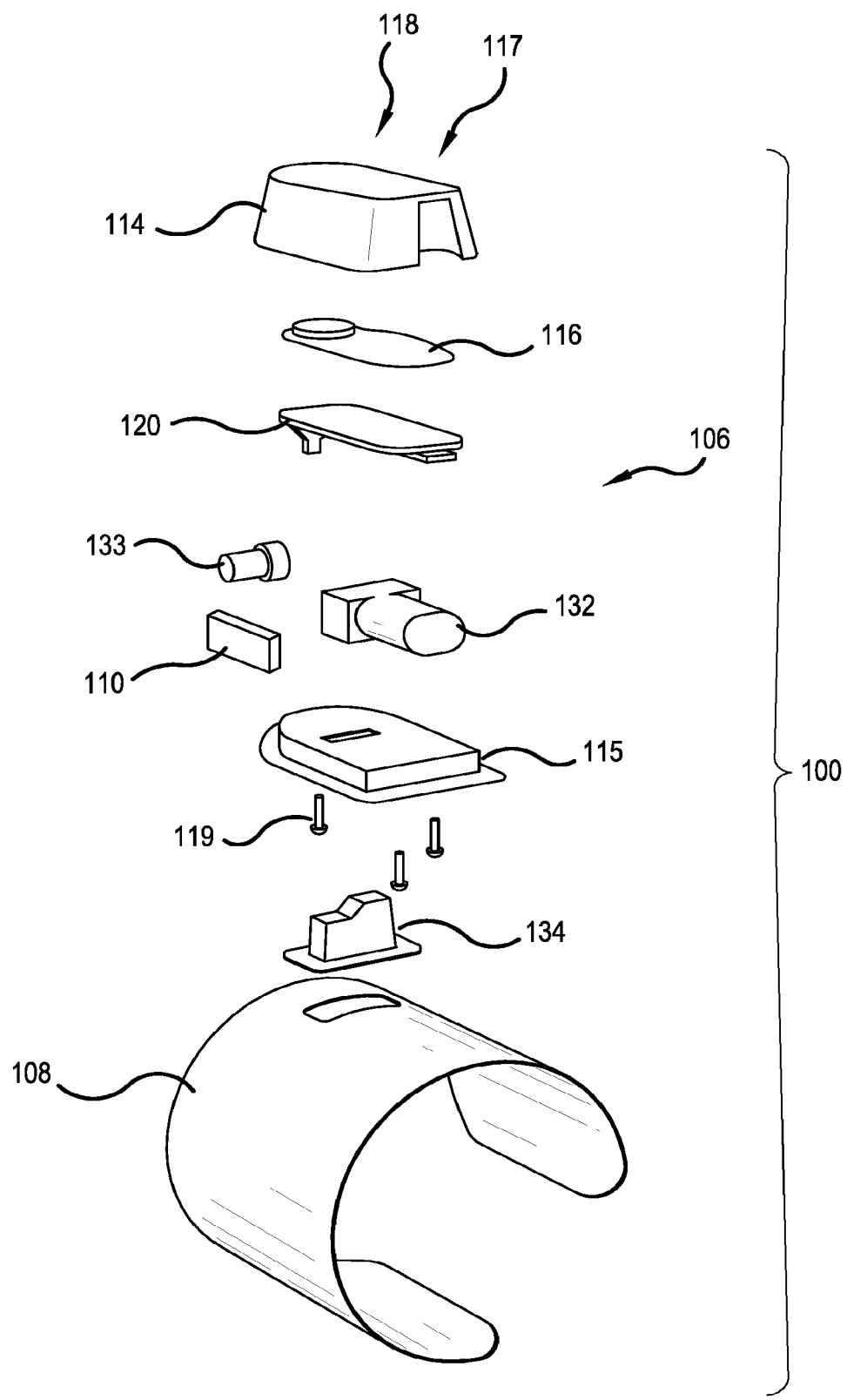
FIG. 4 illustrates an expanded view of the movement unit and the adjustment unit.

The adjuster unit 108 includes at least one of: a spring, a lace, a belt, inflatable tubing, and/or combination thereof. For example, the adjuster unit could comprise an air bladder 108 as shown in FIG. 4. The main air bladder could fit around the wrist and be in fluid communication with additional adjuster units components 108c-108g that comprises inflatable air tubing (108c-108g) as depicted in FIG. 2. It is further contemplated that an alternate embodiment would allow the adjuster unit 108 to selectively compress regions of the body. For example, the fluid communication between the air pump 132 and the adjuster unit 108 can be configured with partitions or a valve system generally indicated at reference numerals 142a-142e in FIG. 2 between the air pump and the adjuster units components 108c-108g such that only the wrist region is compressed or only the fingers are compressed.

Figure 7:
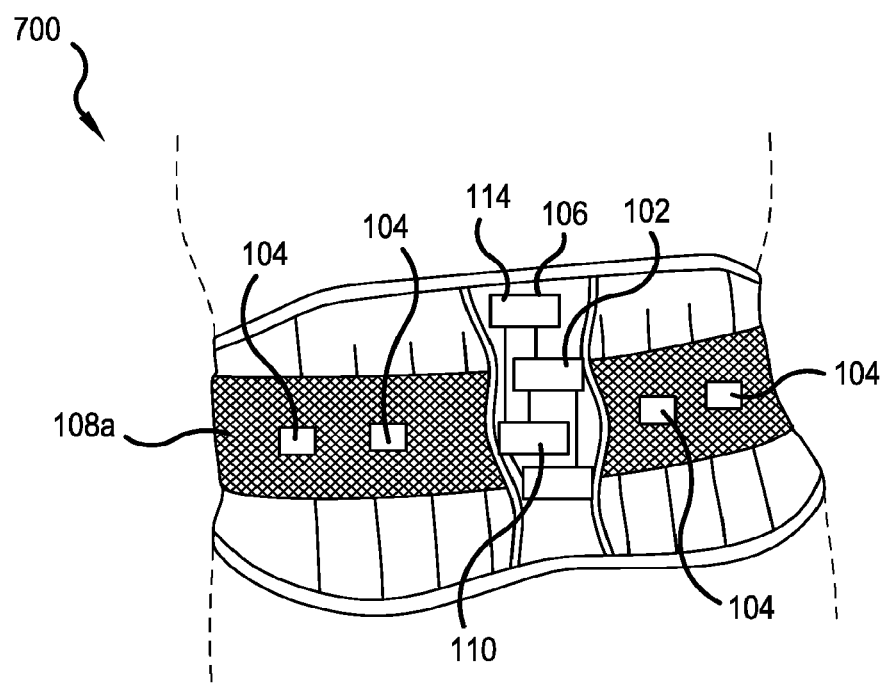
FIG. 7 illustrates another exemplary diagram of the wrap which is removably attached with the lower back of the user to provide compression, and protection, in accordance with at least one embodiment.
Figure 8:
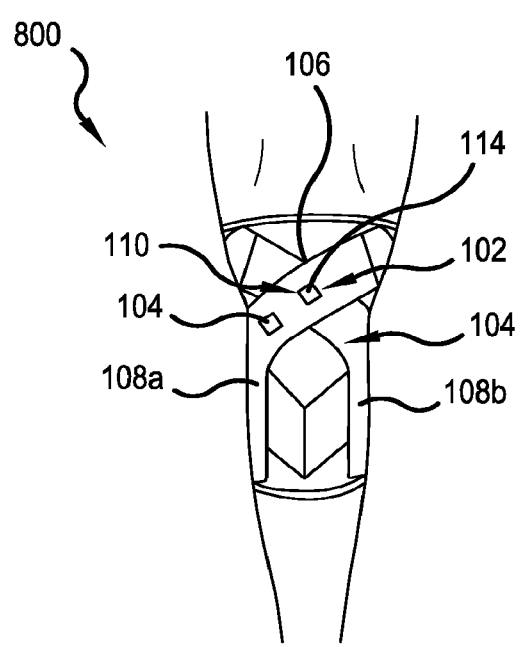
FIG. 8 illustrates another exemplary diagram of the wrap which is removably attached with the knee of the user to provide compression, and protection, in accordance with at least one embodiment.

110 In yet another alternative, the adjustment unit 108 could be configured to apply compression to two regions of the wrap, but at different levels of compression. For example, the adjustment unit component in proximity to the wrist couple be compressed to 85%, while the compression to the fingers may be at 45%. Further, the selective compression of the regions of the wrap can be applied to the wraps covering other regions of the body as shown in FIG. 6, FIG. 7, and FIG. 8.

Figure 5:
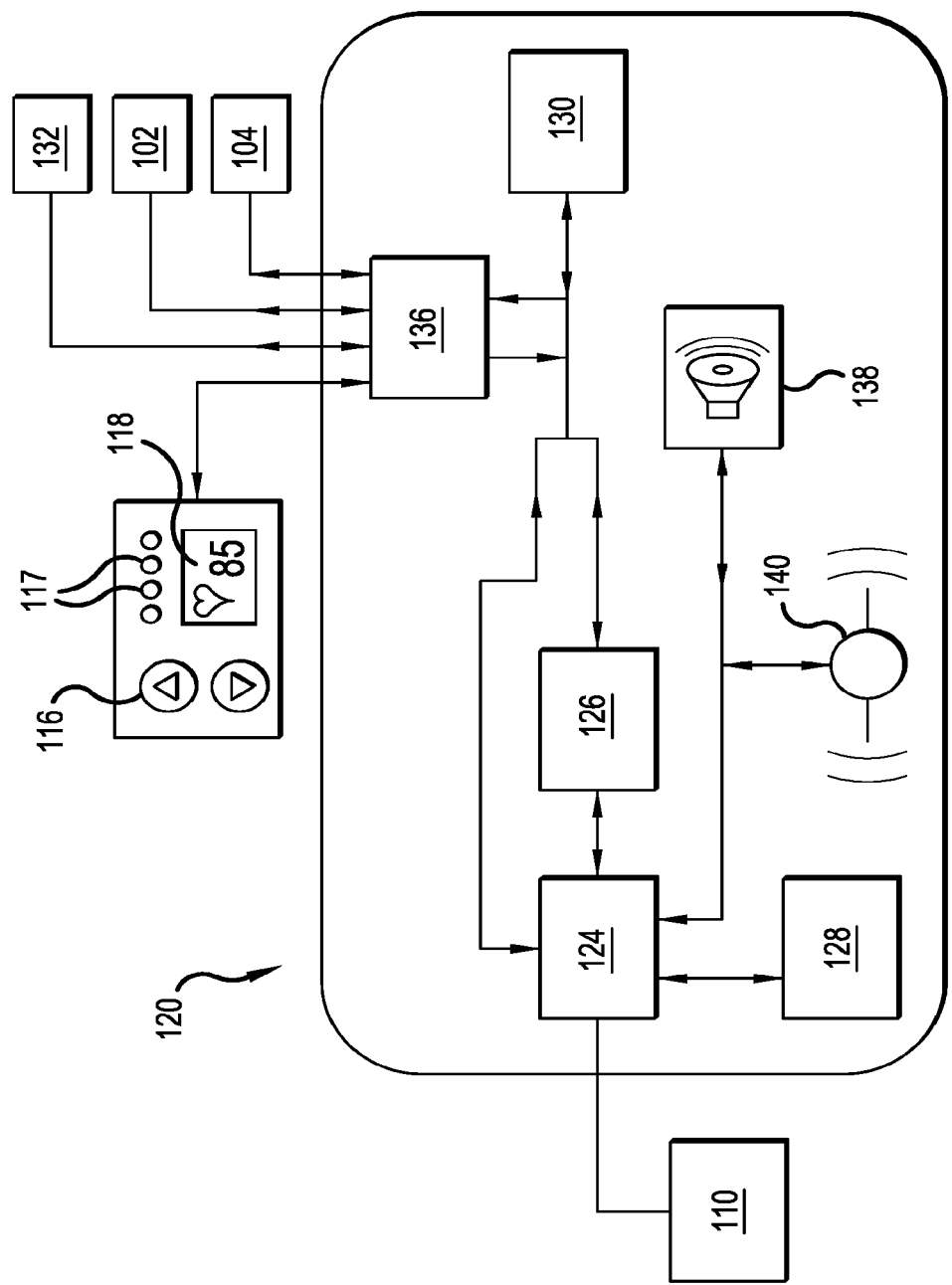
FIG. 5 illustrates a schematic of the circuit board and communication paths to other components of the wrap.

As shown in FIG. 4, an embodiment of the movement unit 106 can be contained in a housing 114 and accompanying base 115. The housing 114 can be used to both protect the movement unit 106 and provide an interface for the user to control the actuation of wrap 100. The housing 114 and base 115 can be coupled to the adjustment unit 108 using screws 119 or another suitable fastener. In an aspect of the wrap 100, the housing 114 can comprise an analog interface comprising a key pad 116. In a further aspect, the keypad 116 can comprise buttons. When buttons are pressed, the user can control the inflation or deflation of the wrap. In addition, the housing can comprise a visual indicator 117 that is in communication and responsive to signals generated by actuated buttons on the keypad 116. For example, when the user presses a button on the keypad 116, an arrangement of light emitting diodes 117 may light up. Further, when the user increases the amount of inflation, the indicator responsively increases the number of illuminated LEDs. Similarly, as the user actuates the keypad 116 to deflate the wrap, the number of illuminated LEDs will decrease. In another embodiment, the indicators 117 can also comprise an auditory component such as an integrated speaker that provides a sequence of sounds for those who may be visually impaired. In yet another aspect, indicator may be vibration action. For example, an oscillating motor 140 could be used to provide similar cues to the user by oscillating in a defined pattern to provide information to the wearer about the wrap's status. In a further aspect, as shown in FIG. 5, the oscillating motor 140 and speaker 138 can also be physically integrated into the structure of the circuit board 120.

In yet another aspect, the keypad can include a digital display 118. The digital display 118 can be configured to toggle between the physiological information measured by the first sensor. For example, the heart rate and blood pressure can be displayed. In another aspect, the information from the second sensor can also be displayed. For example, the percentage of inflation can be displayed to the user.

The movement unit 106 can also comprise a circuit board 120. The circuit board 120 can serve as the communication hub between all of the components of the wrap 100, including but not limited to the first sensor 102, the second sensor 104, the keypad 116, both types of displays (analog and digital), the adjustment unit 108, air pump 132, and power source 110. In a further aspect, the circuit board 120 can comprise a processor 124, memory 126, and antennae 128. The processor 124 can be used to process the inputs received from the keypad and control the outputs to the indicators 117, 118. The processor 124 can also be used control the output on the air pump 132 based on the received input signals through a communication bus 136 on the circuit board 120. The communication bus 136 can be configured as a hub to send and receive signals between the processor 124, first sensor 102, second sensor(s) 104, indicators 117, 118, power source 110 and air pump 132. The processor 124 may also be configured to provide alerts and/or error messages based on the feedback from any received input signals. In one aspect, the alerts can be displayed by the analog indicators 117 or digital indicators 118. In another aspect, the alerts and/or error messages can be provided by a defined sequence by the speaker 138 or oscillating motor 140.

In another aspect, movement unit 106 can comprise a memory 126. The memory 126 can store information about the user's activity. In addition, the communication between the processor 124 and memory 126 can be used to create and store profiles for multiple users of the wrap 100. The information processed and stored and be transmitted to devices. In one embodiment, the wrap 100 can include a USB port 130. Thus, an external processing device can receive data stored in the memory 126 of the wrap. The same USB port 130 can be used as a conduit to provide power to the rechargeable power source 110. The wrap can also comprise an antennae 128 to send and receive data from another device or source. For example, the antennae can be Bluetooth enabled to communicate with the user's cell phone. Further to communicate with other external devices, the antennae 128 can be configured to transmit and receive through radio transmission.

As the wrap is inflated or deflated, air passes from the air pump 132 and passes through the manifold 134 into the adjustment unit 108. In one aspect the adjustment unit 108 may be an air tube or bladder connected to the manifold 134. In a further aspect, the air tube can be a network of tubing interlaced throughout the wrap. The second sensor 104 can be in communication with the adjustment unit 108. In one aspect, the second sensor 104 can be a set of sensors comprising the same type of sensor, measuring the same type of information. The second sensors 104 can be dispersed throughout the wrap to capture dimensional information of the user. For example, the plurality of second sensors 104 can be oriented along the circumference of the wrist. In another aspect, the second sensors 104 can be placed at any location along the wrap. The distances between each sensor 104 can be a known quantity which is stored in the memory 126. Further, the second sensors can be a plurality of linear displacement sensors 104a . . . 104n. The linear displacement sensors can be in communication with each other and the processor 124 in the circuit board. As the wrap inflates or deflates, the displacement of the sensors 104 can provide measurement data to the processor and a respective distance(s) can be calculated. Accordingly, the measurement data from the second sensors 104 and the physiological data from the first sensor can provide data that causes the processor 124 to send a feedback signal to the air pump 132. The feedback data can indicate that a threshold measurement has been exceeded. Accordingly, the feedback signal from the second sensor(s) 104 would initiate an inflation or deflation response for regulating the physiological state of the user. For example, if the user's heart rate slowed from 85 beats per minute to 72 beat per minute, the processor 124 would send a signal to the air pump 132 to decrease the airflow to the adjustment unit 108 from 85% to 45% of the maximum inflation of the wrap.

FIG. 6 illustrates another exemplary diagram 600 of the wrap which is removably attached with the ankle of the user to provide compression, and protection, in accordance with at least one embodiment. The present wrist wraps and ankle wraps inflate to provide compression and protection when the user is working out or not working out. The wrap around the ankle also includes the first sensing unit 102, the second sensing unit 104, the movement unit 106, the adjuster unit 108a, and 108b, and the power source 110. The first sensing unit 102 senses the physiological state of the user's body. The second sensing unit 104 measures the dimension of the ankle of the user. As discussed earlier, alternate embodiment of the wrap in FIG. 6 could include additional adjuster units (108c-108g) that can be oriented to extend to other regions of the ankle: such as the ball of the ankle or arch of the foot.

The movement unit 106 receives the sensed information from the first sensing unit 102, and the second sensing unit 104 to support an inflate mechanism and a deflate mechanism to provide desired compression to the ankle. The adjuster unit 108a, 108b configured with the movement unit 106 to engage or disengage the wrap from the ankle. The power source 110 powers the first sensing unit 102, the second sensing unit 104, the movement unit 106, and the adjuster unit 108a, 108b.

Further, FIG. 7 illustrates another exemplary diagram 700 of the wrap which is removably attached with the lower back of the user to provide compression, and protection, in accordance with at least one embodiment. As mentioned above, the wrap utilized around the lower back also includes the first sensing unit 102, the second sensing unit 104, the movement unit 106, the adjuster unit 108a, and 108b, and the power source 110. The first sensing unit 102 senses the physiological state of the user's body. The second sensing unit 104 measures the dimension of the lower back of the user.

The movement unit 106 receives the sensed information from the first sensing unit 102, and the second sensing unit 104 to support an inflate mechanism and a deflate mechanism to provide desired compression to the lower back. The adjuster unit 108a, 108b configured with the movement unit 106 to engage or disengage the wrap from the lower back. The power source 110 powers the first sensing unit 102, the second sensing unit 104, the movement unit 106, and the adjuster unit 108a, 108b. Similarly, FIG. 8 illustrates another exemplary diagram 800 of the wrap which is removably attached with the knee of the user to provide automatic compression, and protection, in accordance with at least one embodiment.

Figure 9:
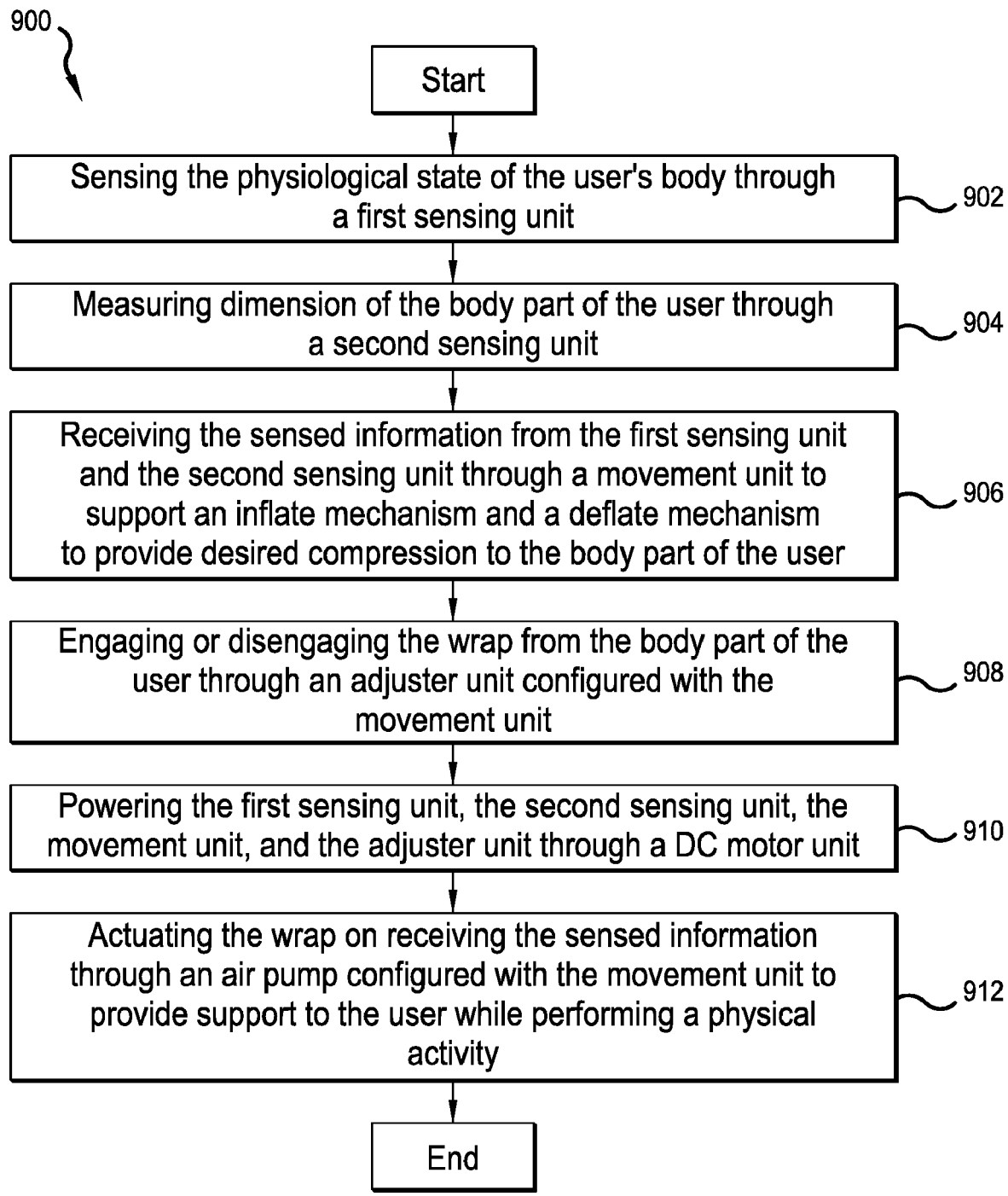
FIG. 9 illustrates the flowchart of the method for providing compression, and protection to at least one of a body part of a user, in accordance with at least one embodiment.

FIG. 9 illustrates the flowchart 900 of the method for providing compression, and protection to at least one of a body part of a user, in accordance with at least one embodiment. The method initiates with the step 902 of sensing the physiological state of the user's body through a first sensing unit. The method further includes the step 904 of measuring dimension of the body part of the user through a second sensing unit. In an embodiment, the body part is selected from at least one of: wrist, ankle, lower back, knee and/or combination thereof. The method further includes the step 906 of receiving the sensed information from the first sensing unit and the second sensing unit through a movement unit to support an inflate mechanism and a deflate mechanism to provide desired compression to the body part of the user. Further the method includes the step 908 of engaging or disengaging the wrap from the body part of the user through an adjuster unit configured with the movement unit. Then the method includes the step 910 of powering the first sensing unit, the second sensing unit, the movement unit, and the adjuster unit through a power source.

Further the method includes the step 912 of actuating the wrap on receiving the sensed information through an air pump configured with the movement unit to provide support to the user while performing a physical activity. Additionally, the user can also actuate the air pump manually. In an embodiment, the power source includes a lithium-ion battery. In another embodiment, the power source can comprise a direct coupling to an electrical outlet.

Thus, the present wrap is a part of the exercise gloves or ankle shoes and automatically inflates and deflates by utilizing an inbuilt air pump which actuates manually or automatically sensing user wrist/ankle size or blood pressure to provide support during physical activity. The present wrap acts as a grip to the ankle/wrist and solves the problem of being a non-wired, non-remote-controlled ankle or wrist compression product. The present wrap gently applies and releases the pressure without using a remote-control device or a wired assistance.

No language in the specification should be construed as indicating any non-claimed element as essential to the practice of the invention.

It will be apparent to those skilled in the art that various modifications and variations can be made to the present invention without departing from the spirit and scope of the invention. There is no intention to limit the invention to the specific form or forms enclosed. On the contrary, the intention is to cover all modifications, alternative constructions, and equivalents falling within the spirit and scope of the invention, as defined in the appended claims. Thus, it is intended that the present invention cover the modifications and variations of this invention, provided they are within the scope of the appended claims and their equivalents.

What is claimed is:

1. A wrap configured to be removably attached with at least one body part of a user to provide compression and protection, the wrap comprising:
   a first sensor on the wrap configured to sense the physiological state of the user's body;
   a second sensor on the wrap configured to measure dimension of the body part of the user;
   a movement unit having an air pump comprising:
      a processor,
      wherein the processor communicates with the first and second sensor and provides a signal to the movement unit air pump to inflate or deflate a portion of the wrap from the sensed information of the physiological state of the user's body and the measured dimension of the body part of the user,
      and
   an adjuster unit having an air bladder, coupled to the movement unit, wherein the movement unit actuates air to the bladder causing it to inflate or deflate accordingly based on the first and second sensor data.

2. The wrap according to claim 1 further comprising a power source coupled to the first sensor, the second sensor, the movement unit, and the adjuster unit.

3. The wrap according to claim 1, wherein the air pump actuates on receiving the sensed information to provide inflate or deflate while performing a physical activity.

4. The wrap according to claim 1, wherein the physiological state of the user's body includes blood pressure, and heart rate.

5. The wrap according to claim 1 coupled with at least one of: an exercise gloves or an ankle shoe.

6. A method for providing compression and protection via a wrap to at least one body part of a user, wherein the wrap comprises: a first sensor, a second sensor, a processor, a movement unit and adjuster unit, the method comprising steps of:
   sensing the physiological state of the user's body through the first sensor;
   measuring dimension of the body part of the user through the second sensor, wherein the body part is selected from at least one of: wrist, ankle, lower back, knee and/or combination thereof;
   providing a movement unit having an air pump receiving the physiological data from the first sensor and measurement data from the second sensor at the processor;
   based on the sensed information from the first sensor and the second sensor, adjusting a compression force of the wrap by inflating or deflating the wrap by the adjuster unit having a bladder, wherein the adjuster unit is coupled to the movement unit and wherein the movement unit actuates air to engage or disengage the portion of the wrap.

7. The method according to claim 6, wherein the physiological state of the user's body includes blood pressure, and heart rate.

8. The method according to claim 6, wherein a power source is a lithium-ion battery.

9. The wrap of claim 1, wherein the adjuster unit further comprises an inflatable air bladder and air tubing, wherein the air bladder is in communication with the air tubing to selectively compress regions of the body part.

10. The wrap of claim 9, wherein the adjuster unit is configured to engage or disengage the wrap from the body part of the user by increasing or decreasing a volume of the inflatable air bladder.

11. The wrap of claim 1, wherein the adjuster unit further comprises components that provides compression to fingers.

12. The method of claim 6, wherein the adjuster unit provides compression to fingers.

13. The wrap of claim 1, further comprising a speaker and an oscillating motor, wherein the speaker and the oscillating motor are in communication with the processor and both the speaker and the oscillating motor are configured to generate an alert.

14. The method of claim 6, further comprising generating an alert based the physiological data received from the first sensor and the measurement data from the second sensor.

* * * * *